(12) United States Patent
Jardret et al.

(10) Patent No.: US 11,517,480 B2
(45) Date of Patent: Dec. 6, 2022

(54) MULTI-LUMEN BRIDGE FOR NEGATIVE PRESSURE WOUND THERAPY SYSTEM

(71) Applicant: DeRoyal Industries, Inc., Powell, TN (US)

(72) Inventors: Vincent Denis Jardret, Powell, TN (US); Jonathan Matthew Cayce, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 451 days.

(21) Appl. No.: 16/364,902

(22) Filed: Mar. 26, 2019

(65) Prior Publication Data

US 2019/0321232 A1    Oct. 24, 2019

Related U.S. Application Data

(60) Provisional application No. 62/647,973, filed on Mar. 26, 2018.

(51) Int. Cl.
*A61F 13/00* (2006.01)
*A61F 13/02* (2006.01)
(Continued)

(52) U.S. Cl.
CPC .... *A61F 13/00068* (2013.01); *A61F 13/0216* (2013.01); *A61M 1/85* (2021.05); *A61M 39/105* (2013.01)

(58) Field of Classification Search
CPC . A61F 13/00068; A61F 13/0216; A61M 1/85; A61M 39/105; A61M 1/90; A61M 2205/75; A61M 1/784; A61M 1/962
See application file for complete search history.

(56) References Cited

U.S. PATENT DOCUMENTS 4,598,004 A   7/1986 Heinecke
7,976,533 B2  7/2011 Larsson
(Continued)

FOREIGN PATENT DOCUMENTS

CN    103781501 B    8/2016

OTHER PUBLICATIONS

The International Searching Authority, Authorized Officer Lee W. Young, Notification of Transmittal of the International Search Report and the Written Opinion of the International Searching Authority, PCT/US2019/024049, dated Jun. 10, 2019.
(Continued)

*Primary Examiner* — Tatyana Zalukaeva
*Assistant Examiner* — Nhu Q. Tran
(74) *Attorney, Agent, or Firm* — Luedeka Neely Group, P.C.

(57) ABSTRACT

A bridge for facilitating delivery of reduced pressure to a wound site includes a reduced pressure lumen configured to be fluidly coupled to a reduced pressure source, a secondary pressure lumen configured to be fluidly coupled to a secondary pressure source, and one or more fluid adapters operable to be connected to a wound dressing disposed at the wound site. The one or more fluid adapters are positioned and configured with respect to the reduced pressure lumen to apply reduced pressure from the reduced pressure lumen to the wound site through the wound dressing and deliver exudate removed from the wound site through the reduced pressure lumen to the reduced pressure tubing. The secondary pressure lumen is fluidly coupled to the reduced pressure lumen to facilitate flow of the exudate removed from the wound site by the reduced pressure source using the secondary pressure source.

17 Claims, 4 Drawing Sheets

(51) Int. Cl.
    *A61M 1/00*         (2006.01)
    *A61M 39/10*       (2006.01)

(56) References Cited

U.S. PATENT DOCUMENTS

| | | |
|---|---|---|
| 8,158,844 B2 | 4/2012 | McNeil |
| 8,814,842 B2 | 8/2014 | Coulthard et al. |
| 9,050,398 B2 | 6/2015 | Armstrong et al. |
| 9,095,470 B2 | 8/2015 | Wilkes |
| 9,180,233 B2 | 11/2015 | Kagan et al. |
| 2005/0004534 A1 | 1/2005 | Lockwood et al. |
| 2006/0015060 A1* | 1/2006 | Oglesby ............... A61M 35/30 604/23 |
| 2010/0069829 A1 | 3/2010 | Hutchinson et al. |
| 2010/0087767 A1* | 4/2010 | McNeil ................. A61M 27/00 602/42 |
| 2012/0271257 A1 | 10/2012 | Coulthard et al. |
| 2013/0310809 A1* | 11/2013 | Armstrong ............. F16L 21/00 604/543 |
| 2014/0066868 A1 | 3/2014 | Freedman et al. |
| 2015/0005678 A1* | 1/2015 | Wall .................... A61H 9/0078 601/9 |
| 2015/0359951 A1 | 12/2015 | Andersen et al. |
| 2016/0106892 A1 | 4/2016 | Hartwell |
| 2017/0182230 A1 | 6/2017 | Ingram et al. |
| 2017/0189236 A1 | 7/2017 | Locke et al. |
| 2019/0290499 A1* | 9/2019 | Askem ................... A61M 1/90 |

OTHER PUBLICATIONS

European Patent Office, European Search Report, EPO Form 1507S, European patent application 19 774 799.1, 80298 Muchich, Germany, dated Dec. 1, 2021.

* cited by examiner

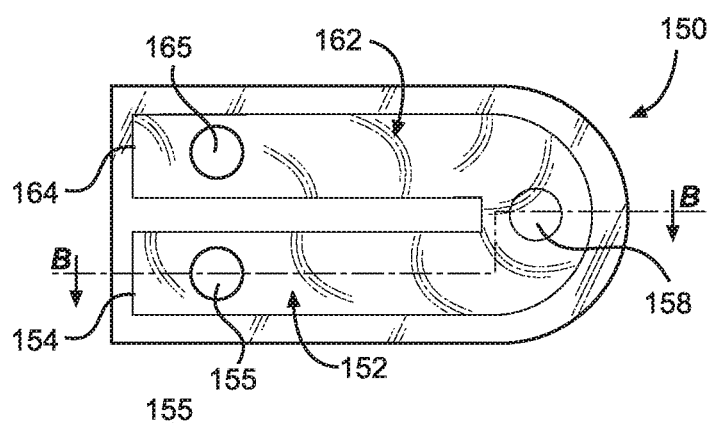
FIG. 4
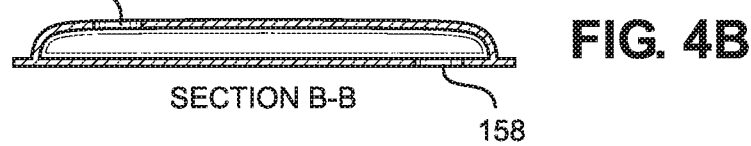
FIG. 4B
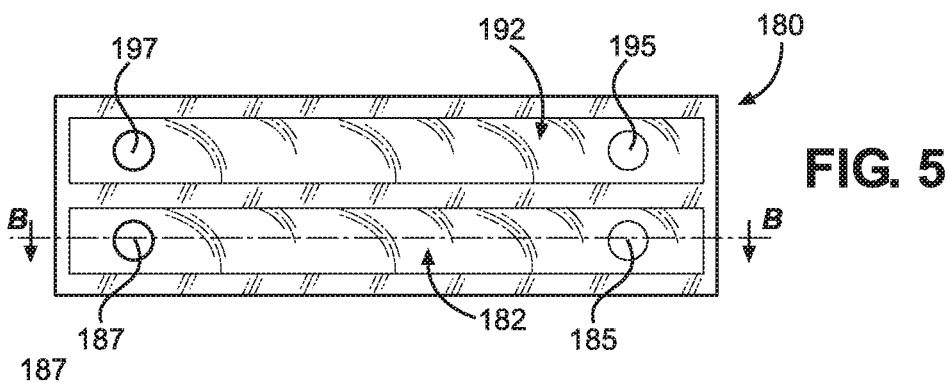
FIG. 5
FIG. 5B
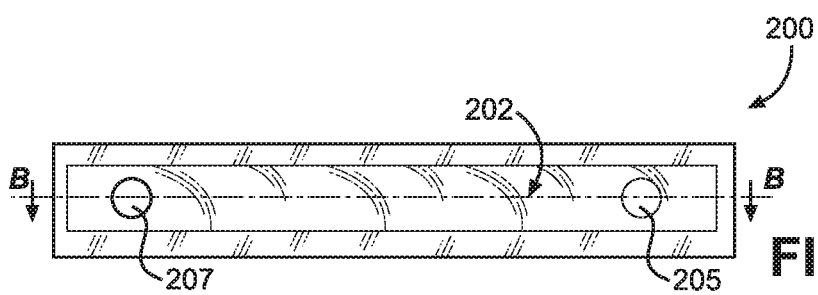
FIG. 6
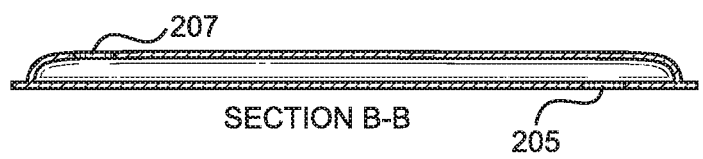
FIG. 6B

MULTI-LUMEN BRIDGE FOR NEGATIVE PRESSURE WOUND THERAPY SYSTEM

CROSS REFERENCE TO RELATED APPLICATION

This application claims priority to U.S. Provisional Application Ser. No. 62/647,973 filed Mar. 26, 2018, entitled "Multi-Lumen Bridge for Negative Pressure Wound Therapy System," the entire contents of which is incorporated herein by reference.

FIELD

This disclosure relates to the field of negative pressure wound therapy. More particularly, this disclosure relates to a bridge for facilitating fluid flow from multiple pressure sources to/from difficult to access wound sites.

BACKGROUND

The primary purpose of negative pressure wound therapy (also referred to as "reduced pressure therapy" or "vacuum therapy" in the medical community) is to apply a reduced pressure (also referred to as "negative pressure" or "vacuum pressure" but will be referred to herein as "reduced pressure") to a wound site to stimulate healing and remove excess exudate from the wound site. The major components of a negative pressure wound therapy system (hereinafter "NPWT system") include a reduced pressure source (e.g., vacuum pump), a waste canister for collecting extracted exudate from the wound site, a wound dressing/enclosure for filling/covering the wound site, and tubing fluidly connecting the wound dressing/enclosure to the reduced pressure source and the canister. The wound dressing typically includes a wound filler such as foam or gauze and a thin film (typically a polyurethane film) adhesively applied to a patient's skin around the wound site and over the wound filler. The thin film creates a substantially sealed enclosure at the wound site. A hole is typically provided in the thin film near the center of the wound for enabling the wound dressing to be fluidly coupled to the reduced pressure source via a "dome" that fluidly connects the tubing to the hole in the thin film.

To assist the reduced pressure source, it has been determined that the presence of an additional air flow in the dome plays a significant role in moving the exudate from the wound site to the canister. Vents to the atmosphere around the dome has traditionally been the source of this additional air flow. However, the use of ambient/environmental air from outside the NPWT system raises air quality concerns. Further, it is difficult to manage the additional air flow in conjunction with the reduced pressure from the reduced pressure source using vents in the dome.

Additionally, the location of a wound site often does not permit convenient placement of a hard, bulky, and/or non-conformable dome over the wound site. Thus, in these circumstances, the dome is either located a distance away from the wound site and a bridge typically made of soft materials is used to fluidly couple the dome to the wound dressing or the dome is omitted entirely and the tubing from the reduced pressure source is directly connected to the bridge. In the former solution for difficult to access wound sites, it has been found that the distance between the bridge and the dome prevents the dual air flow in the dome from having a significant impact in exudate removal from the wound site to the canister. In the latter solution, the desired dual air flow is generally omitted for difficult to access wound sites or a vent is disposed in the bridge or wound dressing, which still has the undesirable effect of introducing environmental air that cannot be effectively managed into the NPWT system as noted above.

What is needed, therefore, is an improved NPWT system bridge for delivering reduced pressure to a wound dressing with a manageable additional air flow to facilitate flow of the exudate from the wound site to the canister. In addition, it is desirable to provide this air flow without introducing ambient air from the surrounding environment.

SUMMARY

The above and other needs are met by a system for facilitating delivery of reduced pressure to a wound site. The system includes a bridge having a reduced pressure lumen, a secondary pressure lumen, and one or more fluid adapters operable to be connected to a wound dressing disposed at the wound site. The reduced pressure lumen includes a first end and a second end with the first end of the reduced pressure lumen configured to be fluidly coupled to reduced pressure tubing that is fluidly coupled to a reduced pressure source. The secondary pressure lumen includes a first end and a second end with the first end of the secondary pressure lumen configured to be fluidly coupled to secondary pressure tubing that is fluidly coupled to a secondary pressure source. The second end of the secondary pressure lumen is fluidly coupled to the second end of the reduced pressure lumen to facilitate flow of exudate removed from the wound site by the reduced pressure source using the secondary pressure source. The one or more fluid adapters are positioned and configured with respect to the reduced pressure lumen to apply reduced pressure from the reduced pressure lumen to the wound site through the wound dressing and deliver exudate removed from the wound site through the reduced pressure lumen to the reduced pressure tubing.

According to certain embodiments, the system further includes a first sealing member, a second sealing member, and a manifold member disposed between the first sealing member and the second sealing member for forming the reduced pressure lumen and the secondary pressure lumen. According to this embodiment, the manifold member includes an opening for fluidly connecting the secondary pressure lumen to the reduced pressure lumen. In some embodiments, the one or more fluid adapters extend through the first sealing member and at least one of the one or more fluid adapters is disposed adjacent to the opening of the manifold member.

According to certain embodiments, the first sealing member is configured to contact skin of a patient with the first sealing member including a moisture permeable membrane for allowing moisture from the patient to transfer into at least one of the reduced pressure lumen and the secondary pressure lumen through the moisture permeable membrane.

According to certain embodiments, the first sealing member is configured to contact skin of a patient with the first sealing member including an adhesive for securing the bridge to the skin of the patient and a release liner for substantially covering the first sealing member prior to securing the bridge to the skin of the patient. In some embodiments, the release liner includes a plurality of perforated sections for providing selective application of the first sealing member to the skin of the patient.

According to certain embodiments, the one or more fluid adapters includes a first fluid adapter disposed adjacent the second end of the reduced pressure lumen for connection to a first connection site of the wound dressing and a second fluid adapter disposed adjacent the second end of the secondary pressure lumen for connection to a second connection site of the wound dressing. According to this embodiment, the secondary pressure lumen is fluidly coupled to the reduced pressure lumen based at least in part on a converged fluid flow path between the first and second connection sites of the wound dressing.

According to certain embodiments, the bridge may further include one or more modular components for connecting the first end of the reduced pressure lumen to the reduced pressure tubing and for connecting the first end of the secondary pressure lumen to the secondary pressure tubing. In some embodiments, the one or more modular components includes a dual lumen extension element having a first lumen for fluidly coupling to the reduced pressure tubing at a first end and to the reduced pressure lumen at a second end and a second lumen for fluidly coupling to the secondary pressure tubing at a first end and to the secondary pressure lumen at a second end. According to this embodiment, the first lumen of the dual lumen extension element may be isolated from the second lumen. In some embodiments, the first lumen includes one or more fluid adapters for connecting the first lumen to a second wound dressing disposed at a second wound site. In some embodiments, the first lumen of the dual lumen extension element includes a fluid adapter disposed between the first end and the second end of the first lumen and the one or more modular components further includes a reduced pressure lumen extension element for fluidly coupling to the fluid adapter of the first lumen of the dual lumen extension element. The reduced pressure lumen extension element of this embodiment includes one or more fluid adapters for connecting the reduced pressure lumen extension element to a second wound dressing disposed at a second wound site.

According another embodiment, the one or more modular components includes a first modular component including a single lumen for fluidly coupling to the secondary pressure tubing at a first end and to the secondary pressure lumen at a second end and a second modular component including a single lumen for fluidly coupling to the reduced pressure tubing at a first end and the reduced pressure lumen at a second end. According to this embodiment, the single lumen may include one or more fluid adapters disposed between the first end and the second end for connecting the second modular component to a second wound dressing disposed at a second wound site. According to yet another embodiment, the one or more modular components include one or more single lumen extension elements for fluidly coupling to the secondary pressure tubing at a first end and to the secondary pressure lumen at a second end or to the reduced pressure tubing at the first end and to the reduced pressure lumen at the second end.

According to another embodiment of the disclosure, the system may further include the reduced pressure source configured to deliver the reduced pressure through the reduced pressure tubing, a canister fluidly coupled with the reduced pressure source and the reduced pressure tubing for receiving exudate collected from the wound site, and the secondary pressure source configured to deliver the secondary pressure through the secondary pressure tubing. In certain embodiments, the system includes a first closed volume disposed between the reduced pressure source and the second end of the reduced pressure lumen of the bridge and a second closed volume disposed between the secondary pressure source and the second end of the secondary pressure lumen of the bridge with the first closed volume and the second closed volume being fluidly connected at the second ends of the reduced pressure lumen and the secondary pressure lumen. In certain embodiments, the first closed volume includes a first pressure sensor and the second closed volume includes a second pressure sensor. In certain embodiments, the system further includes a controller configured to communicate with the secondary pressure source for selectively delivering the secondary pressure to the secondary pressure lumen of the bridge.

According to another embodiment of the disclosure, a system for facilitating delivery of reduced pressure to a wound site is disclosed with the bridge including a reduced pressure lumen configured to be fluidly coupled to a reduced pressure source and a secondary pressure lumen configured to be fluidly coupled to a secondary pressure source at a first end and fluidly coupled to the reduced pressure lumen at a second end to facilitate flow of exudate removed from the wound site by the reduced pressure source using the secondary pressure source. According to this embodiment, at least one of the reduced pressure lumen and the secondary pressure lumen includes a skin contacting surface formed at least in part of a moisture permeable membrane for allowing moisture from the patient to transfer into the reduce pressure lumen or secondary pressure lumen through the moisture permeable membrane.

In certain embodiments, the skin contacting surface includes an adhesive for securing the bridge to the skin of the patient, and the bridge further includes a release liner for substantially covering the skin contacting surface prior to securing the bridge to the skin of the patient. In some embodiments, the release liner includes a plurality of perforated sections for providing selective application of the skin contacting surface to the skin of the patient.

According to yet another embodiment of the disclosure, a system for facilitating delivery of reduced pressure to a wound site includes a bridge having a first sealing member and a second sealing member. The first sealing member includes an inner surface and a skin contacting outer surface. The second sealing member is sealed to a portion of the inner surface of the first sealing member for forming a substantially sealed enclosure having a reduced pressure lumen and a secondary pressure lumen disposed between the first sealing member and the second sealing member. The secondary pressure lumen is fluidly coupled to the reduced pressure lumen to form a fluid flow path within the substantially sealed enclosure. The bridge further includes a first fluid adapter for fluidly coupling the reduced pressure lumen to a reduced pressure source to deliver exudate removed from the wound dressing through the reduced pressure lumen of the fluid flow path, a second fluid adapter for fluidly coupling the secondary pressure lumen to a secondary pressure source such that, when the secondary pressure source is activated, fluid flow from the secondary pressure source delivered through the secondary pressure lumen converges with fluid flow from the reduced pressure source along the fluid flow path to facilitate delivery of the exudate removed from the wound dressing through the reduced pressure lumen, and a third fluid adapter extending through the first sealing member and disposed along the fluid flow path between the first fluid adapter and the second fluid adapter for fluidly coupling the reduced pressure lumen to the wound dressing and for fluidly coupling the secondary pressure lumen to the reduced pressure lumen adjacent to the wound dressing.

In certain embodiments, the first sealing member is formed at least in part of a moisture permeable membrane for allowing moisture from a patient to transfer into the substantially sealed enclosure through the first sealing member. In some embodiments, the first sealing member includes an adhesive for securing the bridge to the patient with the bridge further including a release liner for substantially covering the skin contacting surface prior to securing the bridge to the skin of the patient. In some embodiments, the release liner includes a plurality of perforated sections for providing selective application of the skin contacting surface to the skin of the patient.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 4 depicts an overhead view of a modular connection bridge according to one embodiment of the disclosure;

FIG. 4B depicts a cross-sectional view of the modular connection bridge taken along line B of FIG. 4;

FIG. 5 depicts an overhead view of a multi-lumen extension element according to one embodiment of the disclosure;

FIG. 5B depicts a cross-sectional view of the multi-lumen extension element taken along line B of FIG. 5;

FIG. 6 depicts an overhead view of a single lumen extension element according to one embodiment of the disclosure;

FIG. 6B depicts a cross-sectional view of the single lumen extension element taken along line B of FIG. 6;

DETAILED DESCRIPTION

Figure 1:
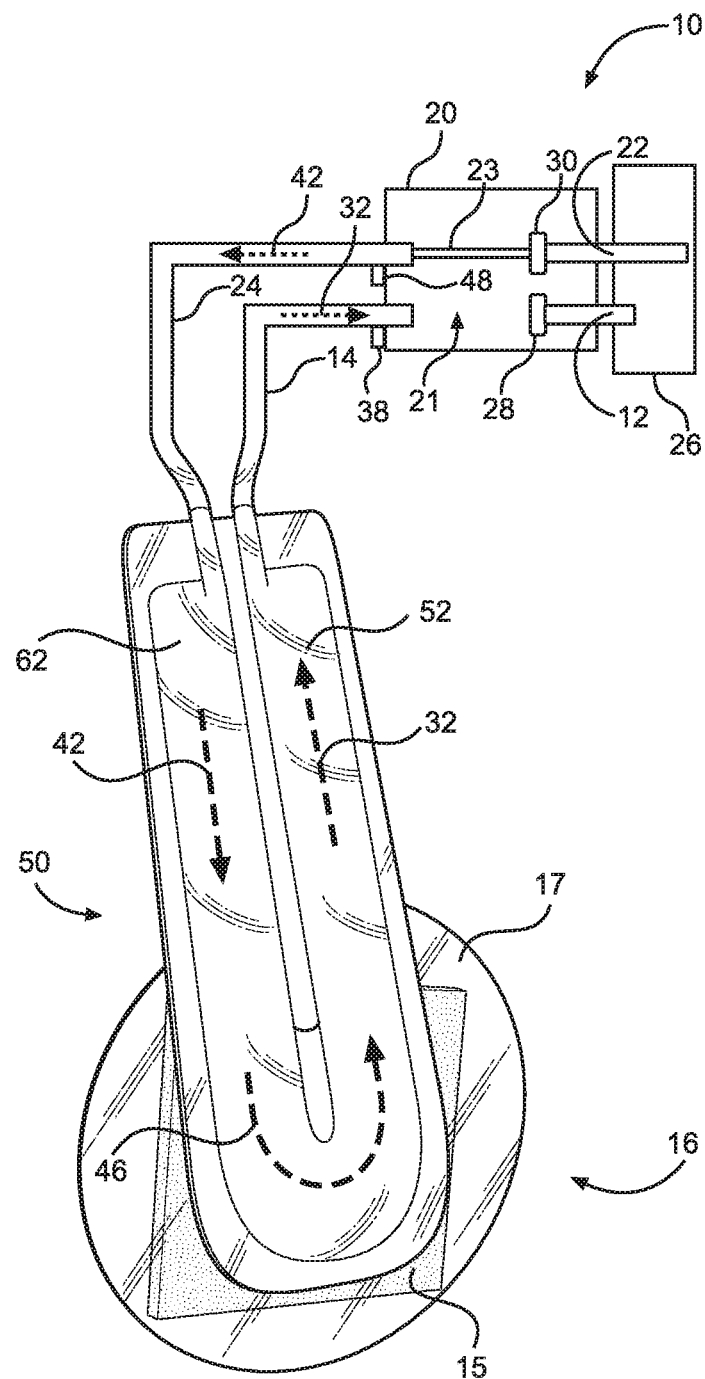
FIG. 1 depicts a somewhat schematic diagram of a NPWT system according to one embodiment of the disclosure.

Referring initially to FIG. 1, the present disclosure is generally directed to a NPWT system 10 having a reduced pressure source 12 configured to deliver reduced pressure through reduced pressure tubing 14 to a wound dressing 16 that is to be disposed at a wound site. As understood in the art, the wound dressing 16 typically includes a foam/gauze material 15 for filling the open wound and a thin film 17 (typically a polyurethane film) adhesively applied to a patient's skin around the wound site for sealing the wound site. A waste canister 20 is fluidly coupled with the reduced pressure source 12 and the reduced pressure tubing 14 for receiving exudate collected from the wound site. A secondary pressure source 22 is configured to deliver a secondary pressure through secondary pressure tubing 24. In certain embodiments, at least a portion of reduced pressure tubing 14 and secondary pressure tubing 24 may be joined together using dual lumen tubing as known in the art. In other embodiments, the reduced pressure tubing 14 and secondary pressure tubing 24 may be entirely separate tubing.

While the reduced pressure tubing 14 and secondary pressure tubing 24 may be connected directly to a wound dressing 16 or sealed wound enclosure disposed at the wound site as described in detail in U.S. patent application Ser. No. 16/235,113, which is commonly assigned to the assignee of the present application and the disclosure of which is incorporated by reference herein in its entirety, the present disclosure is directed to a bridge 50 for fluidly coupling the reduced pressure tubing 14 and secondary pressure tubing 24 to the wound dressing 16. The bridge 50 facilitates delivery of the reduced pressure to wound sites in which placement of a bridge 50 made of soft materials is preferred. While the bridge 50 is explained in more detail below, the bridge generally includes a reduced pressure lumen 52 that is configured to be fluidly coupled to the reduced pressure tubing 14 and a secondary pressure lumen 62 that is configured to be fluidly coupled to secondary pressure tubing 24. The reduced pressure lumen 52 and secondary pressure lumen 62 are fluidly connected to each other within the bridge 50 and/or the dressing 16 such that the secondary pressure is able to facilitate the removal of exudate through the reduced pressure lumen 52 of bridge 50 and the reduced pressure tubing 14 until it is deposited in the canister 20.

For purposes of the present disclosure, it is noted that "fluidly coupled" (or "fluidly coupling") broadly refers to two or more structures or fluid passages being in fluid communication with each other while recognizing the potential for intervening components being used to fluidly connect the particular structures or fluid passages. For example, the waste canister 20 as described above may be referred to as "fluidly coupled" to the wound dressing 16 despite intervening reduced pressure tubing 14 being used to connect the components together. Similarly, the reduced pressure tubing 14 may be referred to as being used for "fluidly coupling" the wound dressing 16 to the reduced pressure source 12 despite the canister 20 being disposed along the fluid flow path between the tubing 14 and the reduced pressure source 12. On the other hand, "fluidly connected" (or "fluidly connecting") may be used to refer to a more direct fluid communication between two components. For example, the reduced pressure lumen 52 and secondary pressure lumen 62 of bridge 50 are typically described herein as being "fluidly connected" when there is a direct fluid communication between the two lumens within the bridge 50.

In certain embodiments, and as depicted in FIG. 1, a single vacuum pump 26 may provide both the reduced pressure source 12 and secondary pressure source 22. According to this embodiment, the inlet of the vacuum pump 26 serves as the reduced pressure source 12 by fluidly connecting the inlet with a collection chamber 21 of canister 20 and also fluidly connecting the reduced pressure tubing 14 with the collection chamber 21 such that fluid/exudate collected from the wound site is deposited in the collection chamber 21 of canister 20. On the other hand, the outlet of the single vacuum pump 26 serves as the secondary pressure source 22 by fluidly coupling the outlet to the secondary pressure tubing 24 via a secondary pressure chamber 23 that traverses the interior of canister 20 while being fluidly isolated from the collection chamber 21 (e.g., a chamber 23 within the canister 20 for fluidly connecting the outlet to the secondary pressure tubing 24 while isolating the secondary pressure generated by the pump outlet from the reduced pressure generated from the pump inlet). According to this embodiment, a first filter 28 is preferably disposed between the pump inlet and the collection chamber 21 and a second filter 30 is preferably disposed adjacent the pump outlet and within secondary pressure chamber 23. The first filter 28 is positioned and configured for protecting the vacuum pump from exudate collected in the collection chamber 21 by preventing exudate from entering the vacuum pump 26 through the pump inlet. The second filter 30 is positioned and configured for removing undesirable particulates generated by the pump outlet 15. Accordingly, using appropriate filters 28 and 30 in combination with the pump inlet as the reduced pressure source 12 and the pump outlet as the secondary pressure source 22, the system 10 of FIG. 1 may be used to create an active circulation of air flow between the canister 20, bridge 50, and the wound dressing 16 using a single vacuum pump 26.

While a single vacuum pump 26 may be used to provide both the reduced pressure source 12 and secondary pressure source 22 as described above and shown in FIG. 1, many other types of secondary pressure sources 22 may be used with bridge 50 of the present disclosure. For example, the secondary pressure source 22 may be a separate chamber filled with fluid under controlled conditions to ensure the quality of the fluid (e.g., filtered air). According to this embodiment, desired fluid flow within system 10 may be created/managed by controlling/managing the pressure difference between the chamber of secondary pressure source 22 and the pressure of canister 20 as described further in the closed system below. According to other embodiments, the secondary pressure source 22 may be a secondary pump for actively pushing fluid to the bridge 50. According to yet another embodiment, the secondary pressure source 22 may include both a chamber filled with fluid under controlled conditions and a secondary pump for actively pushing fluid from the chamber to the bridge 50. In alternate embodiments, secondary pressure source 22 may be a vent to the atmosphere. For example, the secondary pressure source 22 may be a vent in a separate chamber connected to the bridge 50 by secondary pressure tubing 24. The secondary pressure according to this embodiment could be constantly applied to the bridge 50 or controlled by a pump and/or valve (or series of valves). While not as desirable, secondary pressure source 22 of certain embodiments of the present disclosure could even be a vent formed directly in bridge 50 that is fluidly coupled to the secondary pressure lumen 62.

Whether the secondary pressure source 22 is the outlet of the reduced pressure source 12 as depicted in FIG. 1 or a separate chamber/pump as noted above and described in detail in the commonly assigned '113 application, the reduced pressure source 12 generates a first fluid flow path through reduced pressure tubing 14 and reduced pressure lumen 52 (as indicated by arrows 32) while the secondary pressure source 22 generates a second fluid flow path through secondary pressure tubing 24 and secondary pressure lumen 62 (as indicated by arrows 42). According to the first fluid flow path 32, the reduced pressure source 12 is operable to provide primary reduced pressure to the wound dressing 16 such that fluid flows from the wound site to canister 20 via the reduced pressure lumen 52 of bridge 50 and reduced pressure tubing 14. The reduced pressure generated by the reduced pressure source 12 serves both to stimulate healing by applying the reduced pressure to the wound site and removing exudate from the wound site to the canister 20. According to the second fluid flow path 42, the secondary pressure source 22 is operable to provide the secondary pressure to the bridge 50 via the secondary pressure tubing 24 and the secondary pressure lumen 62 of bridge 50 to facilitate removal of the exudate through the reduced pressure lumen 52 and reduced pressure tubing 14 as further described below.

For purposes of the present disclosure, the secondary pressure provided by the secondary pressure source 22 will be greater than the pressure at the connection between the wound dressing 16 and the bridge 50 to prevent exudate from the wound site entering the second fluid flow path 42. Similarly, the secondary pressure will also be greater than the primary reduced pressure generated by the reduced pressure source 12 within the first fluid flow path 32. Accordingly, as the second fluid flow path 42 is fluidly connected to the first fluid flow path 32 via the bridge 50 and the pressure of the second fluid flow path 42 is greater than the pressure of the first fluid flow path 32, fluid from the second fluid flow path 42 is pushed into the first fluid flow path 32 (as indicated by arrow 46 in the bridge 50 and referred to herein as a "converged fluid flow path") when both the reduced pressure source 12 and secondary pressure source 22 are activated.

The converged fluid flow path 46 may be used to facilitate flow of the exudate from the wound site to the canister 20 through the first fluid flow path 32. In other words, activation of the secondary pressure source 22 (such as with a controller connected to the secondary pressure source 22) should prevent or otherwise reduce blockage in the reduced pressure lumen 52 of bridge 50 and the reduced pressure tubing 14, which would require intervention of the nurse and an unnecessary dressing 16 and/or bridge 50 change for the patient as a result of the blockage. For example, according to certain embodiments, the reduced pressure source 12 may be configured to deliver a reduced pressure of −125 mmHg to the wound dressing 16 via the first fluid flow path 32 while the secondary pressure source 22 may be configured to deliver a reduced pressure of −80 mmHg to the bridge 50 via the second fluid flow path 42. Thus, when both the reduced pressure source 12 and secondary pressure source 22 are activated, the second fluid flow path 42 having a pressure of −80 mmHg will converge with the first fluid flow path 32 having a pressure of −125 mmHg. The converged fluid flow path 46 will then have a greater pressure than the −125 mmHG generated by the reduced pressure source 12 to facilitate flow from the wound site 16 to the canister 20 through the first fluid flow path 32.

In preferred embodiments, the reduced pressure source 12 will be configured to apply a reduced pressure to the wound site of between about −5 mmHg to about −200 mmHg, and most preferably between about −40 mmHg to about −125 mmHg. The secondary pressure source 22 is then configured to apply a pressure to the bridge 50 that is greater than the pressure applied to the wound site by the reduced pressure source 12. In preferred embodiments, the secondary pressure will be between about 1 mmHg to about 760 mmHg above the pressure applied at the wound site by the reduced pressure source 12, more preferably about 1 mmHg to about 740 mmHg above the pressure applied at the wound site, and most preferably about 5 mmHg to about 40 mmHg greater than the pressure applied at the wound site.

According to preferred embodiments described herein, fluid flow in the first fluid flow path 32, the second fluid flow path 42, and/or the converged fluid flow path 46 is created/ managed using two or more closed volumes that are fluidly connected by bridge 50. As a result of using two fluidly connected closed volumes to create/control the fluid flow within the system 10, the fluid flow is generated/managed without requiring any type of venting arrangement to produce or manage the fluid flow of the first and second fluid flow paths 32, 42. In other words, while the present disclosure may provide venting of air to the atmosphere to release pressure within the system, the fluid flow of the fluid flow paths 32, 42 described herein are able to be controlled independently of pressure inside or outside the system by controlling the two fluidly connected closed volumes instead of requiring the introduction or release of outside air to generate/manage the fluid flow paths. Thus, for purposes of the present disclosure, the phrase "closed volume" refers to a portion of the NPWT system that does not permit any transfer of air or fluid from outside the system (i.e., environmental air) into the system while fluid flow is activated in the fluid flow path of the particular closed volume. Similarly, a "closed system" refers to a NPWT system having two or more fluidly connected closed volumes in which the system as a whole does not permit any transfer of outside air or fluids into the system (other than exudate fluids removed from the wound site) while fluid flow is activated in the fluid flow paths 32 and 42.

Referring still to FIG. 1, a first closed volume of NPWT system 10 of this embodiment includes the reduced pressure source 12 in fluid communication with the canister 20, a sealed wound dressing 16, reduced pressure tubing 14, and reduced pressure lumen 52 of bridge 50. The secondary pressure source 22, secondary pressure tubing 24, and secondary pressure lumen 62 of bridge 50 forms the second closed volume of NPWT system 10. As a result of both the reduced pressure source 12 and the secondary pressure source 22 being fluidly connected within the bridge 50, the first closed volume is fluidly connected to the second closed volume such that fluid flow between the two closed volumes can be managed without introduction of environmental air from outside the closed system 10.

According to another aspect of the system 10 exemplified in FIG. 1 and described above, a first pressure sensor 38 may be disposed along the first fluid flow path 32 while a second pressure sensor 48 may be disposed along the second fluid flow path 42. In this regard, a pressure measured at one end of a fluid flow path should be substantially equal to the pressure at the other end of the fluid flow path so long as very little to no liquid/exudate is present in the fluid flow path and the inside diameter to length ratio of the fluid flow path is not too small. As result, when the secondary pressure source 22 is inactive, or the second fluid flow path 42 is otherwise fluidly isolated from any secondary pressure generated from the secondary pressure source 22 (e.g., a valve in a closed position is disposed between the secondary pressure source and the second pressure sensor), the second pressure sensor 48 may be used to measure the primary reduced pressure being applied to the wound dressing 16 by the reduced pressure source 12 given that there should be little to no fluid in the second fluid flow path 42.

When the reduced pressure source 12 and secondary pressure source 22 are both activated, various operating conditions of the closed system 10 may be determined by comparing the pressure readings from the first pressure sensor 38 with the pressure readings from the second pressure sensor 48. In particular, the monitoring of the pressure readings from the two pressure sensors may provide information regarding the amount of exudate being delivered from the wound dressing 16 to the canister 20 via the first fluid flow path 32. For example, a small difference between the readings of the two pressure sensors would indicate a small amount of exudate is being delivered to the canister 20 via the first fluid flow path 32 while a greater difference between the pressure readings would indicate a larger amount of exudate in the first fluid flow path 32. In other words, when the pressures of the first fluid flow path 32 and second fluid flow path 42 are the same or substantially similar during activation of both the reduced pressure source 12 and the secondary pressure source 22, this indicates that there should be a relatively small amount of exudate (if any) flowing from the wound dressing 16 to the canister 20 because the secondary pressure from the second fluid flow path 42 has been able to converge with the reduced pressure from the first fluid flow path 32 to form a converged fluid flow path 46 having a similar pressure along the entirety of the converged path. However, when there is a larger amount of exudate in the first fluid flow path 32, the pressure of the first fluid flow path 32 will be substantially different than the pressure of the second fluid flow path 42 because the second fluid flow path 42 was not able to easily converge with the first fluid flow path 32 due to the existence of significant exudate in the first fluid flow path 32. Depending on how great the difference between the pressure readings, it might also be determined that (1) a blockage condition exists in the first fluid flow path 32 and/or (2) a fill condition exists in canister 20 where the canister 20 is close to being filled with exudate.

Figure 2A:
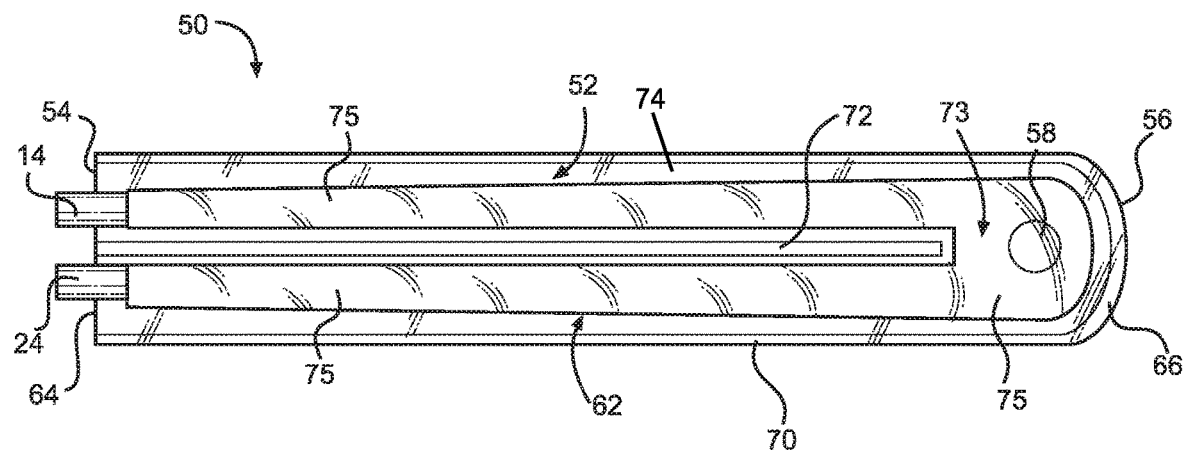
FIG. 2A depicts a bottom cross-sectional view of a multi-lumen bridge with side-by-side lumens according to one embodiment of the disclosure.

Referring to FIG. 2A, a bottom cross-sectional view of a bridge 50 as generally shown in FIG. 1 is depicted with a reduced pressure lumen 52 and secondary pressure lumen 62 arranged in a side-by-side configuration. As shown, reduced pressure lumen 52 includes a first end 54 and a second end 56. The reduced pressure lumen 52 is fluidly coupled to the reduced pressure tubing 14 adjacent its first end 54. The secondary pressure lumen 62 similarly includes a first end 64 and a second end 66 with the secondary pressure lumen 62 being fluidly coupled to the secondary pressure tubing 24 adjacent its first end 64. At their respective second ends 56 and 66, the reduced pressure lumen 52 and secondary pressure lumen 62 are fluidly connected to facilitate flow of the wound exudate as described above with respect to FIG. 1 when the secondary pressure source 22 is activated. As shown, a foam/gauze material 75 may be disposed within the reduced pressure lumen 52 and/or secondary pressure lumen 62. With reference to FIG. 2A, the foam 75 may be unitary and, thus, shaped to conform to the fluidly connected lumens 52, 62. In alternate embodiments, the foam 75 may be separated into separate sections.

With continued reference to FIG. 2A, bridge 50 further includes a fluid adapter 58 for connecting to wound dressing 16 (though fluid adapter 58 would technically be shown in a bottom view of FIG. 2A, fluid adapter 58 is shown in the cross-sectional view of FIG. 2A and other embodiments shown herein to depict the positioning of the adapters with respect to the lumens of the bridge). The fluid adapter 58 is positioned and configured with respect to the reduced pressure lumen 52 to apply reduced pressure generated from the reduced pressure source 12 to the wound site through the wound dressing 16 and deliver exudate removed from the wound site through the adapter 58 to the reduced pressure lumen 52 of the bridge 50. It should be understood that fluid adapter 58, as well as other fluid adapters and connection points described herein, may take various forms for fluidly connecting two conduits or passages as generally known in the art. In certain embodiments, fluid adapter 58 is simply an aperture or female type receiver for fluidly coupling to a corresponding aperture or male adapter protruding from the wound dressing 16. In other embodiments, fluid adapter 58 of bridge 50 may be in the form of a small tube or other male type part for fluidly coupling to a corresponding female type receiver of the wound dressing 16. Similarly, fluid adapter 58 may be a separate component having a first end configured to be fluidly connected to the bridge 50 and a second end configured to be fluidly connected to the dressing 16.

In certain embodiments, bridge 50 could include a plurality of fluid adapters 58 for fluidly coupling the bridge 50 to a wound dressing 16 at a plurality of points along the dressing 16 or for fluidly coupling the bridge 50 to a plurality of wound dressings 16 and/or wound sites. For example, depending on the location of distinct wound sites of a patient and the length of the reduced pressure lumen 52 of bridge 50, a plurality of fluid adapters 58 could be disposed along the length of the reduced pressure lumen 52 for fluidly coupling the bridge 50 to a plurality of wound sites. In other embodiments, the bridge 50 could be fluidly coupled at two or more points to the same wound dressing 16. For example, bridge 50 may include a first fluid adapter 58 adjacent the second end 66 of the secondary pressure lumen 62 and a second fluid adapter 58 adjacent the second end 56 of the reduced pressure lumen 52. In this latter embodiment, the fluid provided by the secondary pressure source 22 may have a particular composition chosen to serve a specific purpose during the wound therapy treatment given that the secondary pressure will be delivered to the wound dressing 16 instead of just the bridge 50. For example, air delivered to the wound dressing 16 from the secondary pressure source 22 may have an increased oxygen content, specific moisture level, and/or specific pH level depending on the desired treatment of the wound site. Further, in this embodiment in which both the secondary pressure from the secondary pressure source 22 and reduced pressure from the reduced pressure source 14 are delivered to the wound dressing 16 via a plurality of fluid adapters 58, the converged fluid path 46 described above may occur within the wound dressing 16 instead of or in addition to the bridge 50.

It has been determined that improved exudate removal has been observed if the point in which the first fluid path 32 converges with the second fluid path 42 is near the wound site. Thus, in preferred embodiments, and particularly in situations in which the bridge 50 is being fluidly coupled to only one wound site, the one or more fluid adapters 58 are preferably positioned adjacent the area of the bridge 50 in which the reduced pressure lumen 52 and secondary pressure lumen 62 are fluidly connected. In other words, the connection between the bridge 50 and the wound dressing 16 is preferably positioned at the point in which the fluid flow paths 32 and 42 of FIG. 1 converge to form the converged fluid flow path 46. Thus, in the side-by-side embodiment of FIG. 2A, the bridge 50 is preferably in a "U" shape with the connection between the bridge 50 and the wound dressing 16 being positioned near the midpoint of the "U" where the reduced pressure lumen 52 and secondary pressure lumen 62 converge. Similarly, in embodiments in which multiple wound sites are to be treated, the bridge 50 is preferably connected to the dressing 16 of the most critical wound site to be treated such that converged fluid flow path 46 occurs adjacent the most critical wound site.

Figure 3:
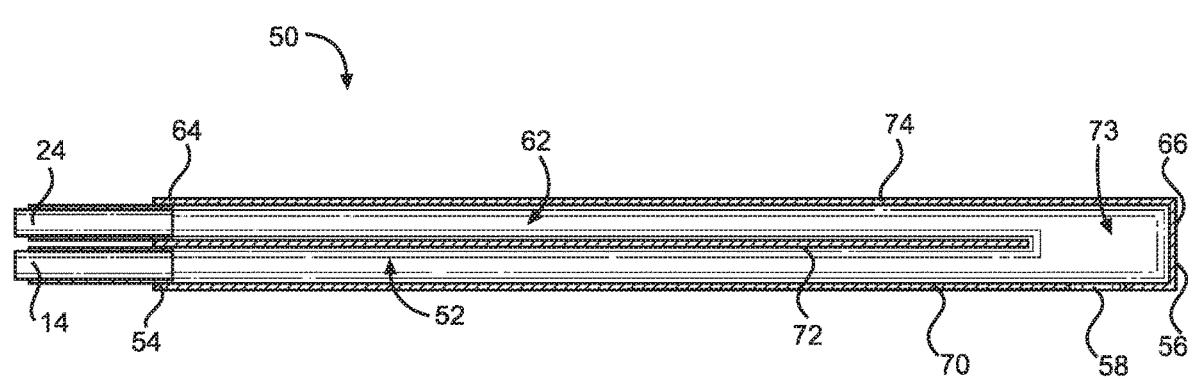
FIG. 3 depicts a side cross-sectional view a multi-lumen bridge with top and bottom lumens according to another embodiment of the disclosure.

Referring to FIG. 3, a side cross-sectional view of another embodiment of bridge 50 is depicted with the reduced pressure lumen 52 and secondary pressure lumen 62 positioned with one on top of the other as compared to the side-by-side arrangement of FIG. 2A. To connect the bridge 50 to a wound dressing 16, the one or more fluid adapters 58 are disposed in the bottom surface of the lower lumen. According to this embodiment, reduced pressure lumen 52 is preferably positioned below the secondary pressure lumen 62 such that the reduced pressure lumen 52 would be adjacent the skin of the patient when the bridge 50 is being used. Thus, the fluid adapter 58 of this embodiment is positioned in the bottom surface of the reduced pressure lumen 52 as depicted in FIG. 3.

Referring to both FIG. 2A and FIG. 3, the reduced pressure lumen 52 and secondary pressure lumen 62 are preferably formed by a first sealing member 70, a second sealing member 74 (not shown in the bottom cross-sectional view of FIG. 2A), and a manifold member 72 disposed between the first sealing member 70 and the second sealing member 74 for forming the reduced pressure lumen 52 and the secondary pressure lumen 62. According to the embodiment of FIG. 2A, the first sealing member 70 and second sealing member 74 are preferably thin polyurethane film layers sealed together both around their peripheries for forming a substantially sealed enclosure and along an inner portion of the sealing members 70, 74 for separating the sealed enclosure into the reduced pressure lumen 52 and the secondary pressure lumen 62. Thus, according to this embodiment, the manifold member 72 is formed by sealing portions of the inner surfaces of the sealing members 70, 74 together. On the other hand, according to the embodiment of FIG. 3, the manifold member 72 is a separate sealing member of bridge 50 disposed between the first and second sealing members 70, 74 such that the reduced pressure lumen 52 is disposed between the first sealing member 70 and the manifold member 72 while the secondary pressure lumen 62 is disposed between the second sealing member 74 and the manifold member 72. For purposes of the disclosure, the first sealing member 70 and second sealing member 74 are referred to as "sealing members" because they form walls that seal the bridge 50 from the outside environment. The manifold member 72 is referred to as a manifold member because it separates the sealed enclosure formed by the first and second sealing members 70, 74 into respective lumens 52, 62. In both embodiments, the manifold member 72 then includes an opening 73 to fluidly connect the reduced pressure lumen 52 and secondary pressure lumen 62 within bridge 50 for forming a fluid flow path between the reduced pressure lumen 52 and the secondary pressure lumen 62. Referring to the embodiment of FIG. 3, the one or more fluid adapters 58 are disposed in the first sealing member 70 preferably below the opening 73 of the manifold member 72 (i.e., along the fluid flow path of the reduced pressure lumen 52 and the secondary pressure lumen 62). On the other hand, with reference to the embodiment of FIG. 2A, the one or more fluid adapters 58 would preferably be disposed in a bottom sealing member generally aligned with the opening 73 of the manifold member 72.

In certain embodiments, the first sealing member 70 described above may also be referred to as the skin contacting surface given that it is intended to be disposed at least in part against the skin of a patient during use. In certain embodiments, and when the first sealing member 70 is intended to be the skin contacting surface of bridge 50, at least the first sealing member 70 includes a moisture permeable membrane for allowing moisture from the patient to transfer into at least one of the reduced pressure lumen 52 and the secondary pressure lumen 62 through the moisture permeable membrane. For example, with reference to the side-by-side configurations of FIGS. 1-2, the first sealing member 70 is intended to contact the skin of the patient when securing the bridge 50 to a wound dressing 16. Thus, in this embodiment, the first sealing member 70 is formed of a polyurethane film that is moisture permeable for allowing moisture from the patient to be absorbed through the first sealing member 70 such that it can be absorbed by foam 75 within the bridge 50 and/or carried away from the bridge 50 by the reduced pressure source 12. Similarly, with reference to the embodiment of FIG. 3, the first sealing member 70 is the bottom sealing member that contacts the skin of the patient and includes the moisture permeable membrane for absorbing moisture to be transferred from the skin of the patient to the bottom lumen (shown as reduced pressure lumen 52 in FIG. 3) of bridge 50.

Figure 2B:
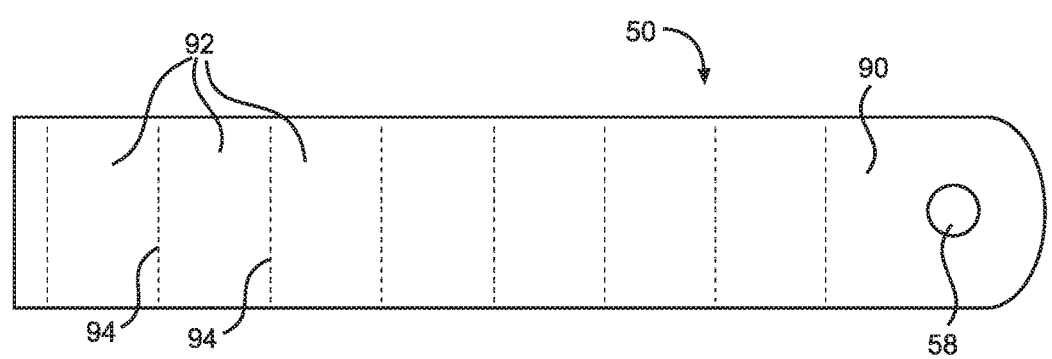
FIG. 2B depicts a bottom view of the multi-lumen bridge of FIG. 2A with a release liner secured to a bottom sealing member of the bridge according to one embodiment of the disclosure.

In certain embodiments, the first sealing member 70 may also include an adhesive for securing bridge 50 to the skin of the patient. According to this embodiment, a release liner may be provided over the adhesive portions of the first sealing member for covering the adhesive prior to securing the bridge 50 to the skin of the patient. With reference to FIG. 2B, which depicts the bridge 50 of FIG. 2A with a release liner 90 covering the first sealing member 70, the release liner 90 preferably includes a plurality of sections 92 separated by perforations 94. Thus, according to this embodiment, a nurse or other caregiver can selectively remove liner 90 from desired sections 92 for selective application of the adhesive of the first sealing member 70 to the skin of the patient.

According to another aspect of the disclosure, and with reference to FIGS. 4-9, bridge 100 may be formed of a plurality of modular components. As shown in FIG. 4, each modular bridge 100 includes a connection bridge 150 generally similar to bridge 50 of FIGS. 1-3. Thus, connection bridge 150 includes a reduced pressure lumen 152 and a secondary pressure lumen 162. The reduced pressure lumen 152 and secondary pressure lumen 162 are fluidly connected within the connection bridge 150. One or more fluid adapters 158 are disposed adjacent the area in which the lumens 152, 162 are fluidly connected for fluidly connecting the connection bridge 150 to a wound dressing. In certain embodiments, first end 154 of the reduced pressure lumen 152 and first end 164 of the secondary pressure lumen 162 may be connected directly to the reduced pressure tubing 14 and secondary pressure tubing 24 using respective fluid adapters 155, 165. However, in other embodiments, connection bridge 150 includes further modular components depending on the patient needs such as the length of bridge 100 being desired, the number of wound sites being fluidly coupled to the pressure sources by bridge 100, and the location of the wound sites.

Similar to fluid adapter 58 described above, the fluid adapters 155, 165 for connecting connection bridge 150 to other modular components described below may take numerous forms so long as they allow a sealed fluid connection between the desired components for maintaining the desired fluid flow paths 32, 42. Further, the location of the connection points may vary. For example, with reference to FIG. 4B, fluid adapter 155 is in the form of an aperture positioned in the top of the reduced pressure lumen 152 adjacent end 154. However, in other embodiments, the fluid adapter 155 could be an aperture formed directly into the end 154 or a male engaging member that protrudes from end 154. It should also be understood that the skin contacting portions of the modular components could include a moisture permeable membrane and/or adhesive as described above with respect to the embodiments of FIGS. 2-3.

With reference to FIG. 5, a dual lumen extension element 180 may be used when it is desired to extend the length of the reduced pressure lumen 152 and secondary pressure lumen 162 of connection bridge 150. Thus, dual lumen extension element 180 includes a first lumen 182 having fluid adapters 185, 187 adjacent opposing ends of the first lumen 182. With reference to FIG. 5B, fluid adapter 185 is disposed in the bottom surface of the first lumen 182 for fluidly connecting the first lumen 182 with the reduced pressure lumen 152 of connection bridge 150 via the fluid adapter 155 shown in FIG. 4. Fluid adapter 187 may then be used to fluidly connect the first lumen 182 to another modular component or to the reduced pressure tubing 14. Dual lumen extension element 180 further includes a second lumen 192 that is operable to be fluidly connected to the secondary pressure lumen 162 of connection bridge 150 using fluid adapter 195 while being fluidly connected to another modular component or the secondary pressure tubing 24 using fluid adapter 197. As dual extension element 180 is intended to just extend the first and second fluid flow paths 32, 42 while the connection bridge 150 provides the converged flow path 46, first lumen 182 and second lumen 192 of the dual lumen extension element 180 are preferably fluidly isolated from each other as depicted in FIG. 5.

Referring to FIG. 6, another modular component may be provided with a single lumen 202 to provide a single lumen extension element 200. Single lumen extension element 200 may be used to extend either reduced pressure lumen 152 or secondary pressure lumen 162 of connection bridge 150 by connecting fluid adapter 205 to one of fluid adapter 155 or 165 of connection bridge 150 (or to a fluid adapter of an intervening modular component if single lumen extension element is not connected directly to connection bridge 150). For example, if it is desired to extend the secondary pressure lumen 162 before connecting it to the secondary pressure tubing 24 without extending the reduced pressure lumen 152 in a similar direction as shown below with respect to FIG. 9, single lumen extension element 200 may be fluidly connected to the secondary pressure lumen 162 of connection bridge 150 via connecting fluid adapter 205 of the single lumen extension element 200 to fluid adapter 155 of the connection bridge 150. According to embodiments in which the wound dressing 16 includes multiple connection points, single lumen extension element 200 may also be used to fluidly couple one of the connecting points of the wound dressing 16 to the reduced pressure tubing 14 while another single lumen extension element 200 is used to fluidly couple the secondary pressure tubing 24 to a second connecting point of the wound dressing 16.

Figure 7:
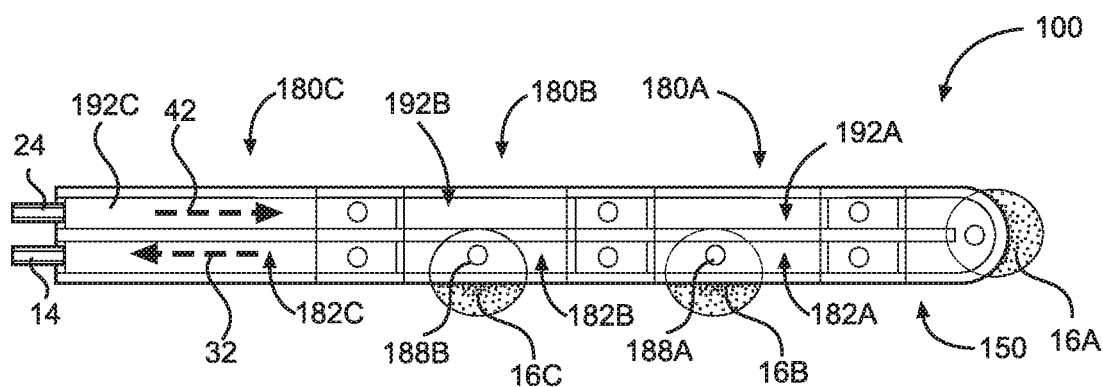
FIG. 7 depicts a cross-sectional view of a modular bridge according to one embodiment of the disclosure.
Figure 8:
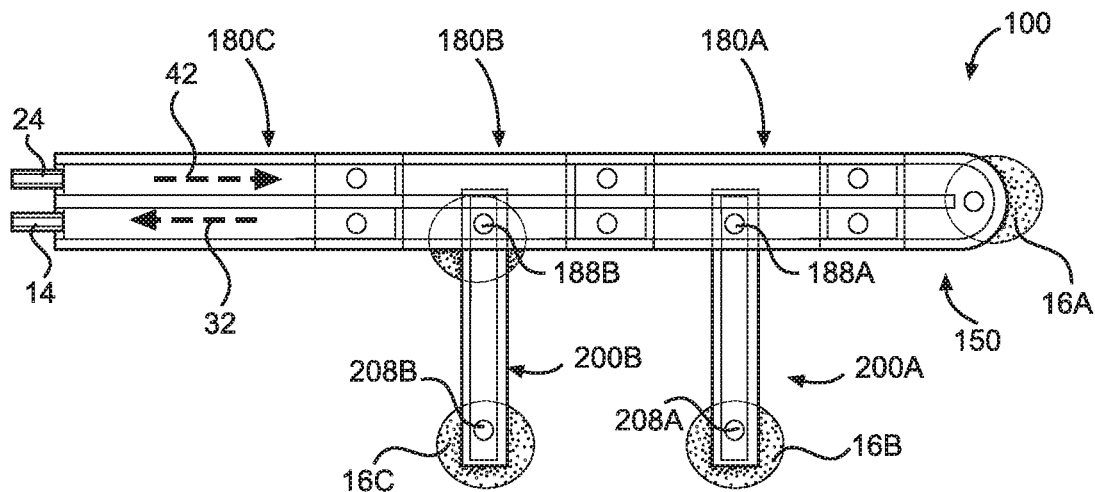
FIG. 8 depicts a cross-sectional view of a modular bridge according to another embodiment of the disclosure.
Figure 9:
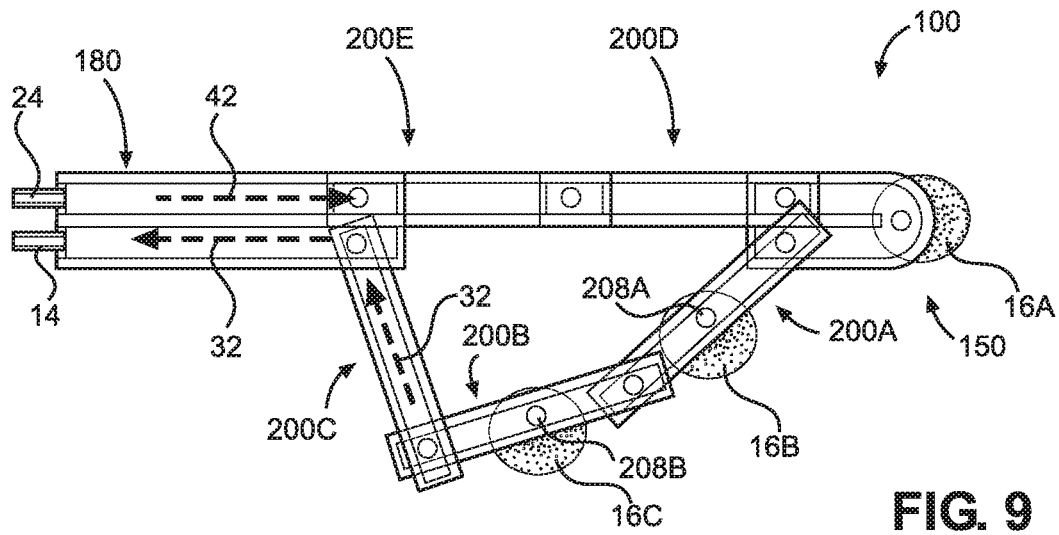
FIG. 9 depicts a cross-sectional view of a modular bridge according to yet another embodiment of the disclosure.

As exemplified in FIGS. 7-9, the modular components described above may be used to provide varying setups for a bridge 100 connecting reduced pressure tubing 14 and secondary pressure tubing 24 to a plurality of wound dressings 16A, 16B, 16C. For example, with reference to FIG. 7, connection bridge 150 is fluidly connected to wound dressing 16A such that the converged fluid path as described above occurs as close as possible to wound dressing 16A. Wound dressing 16A will typically be the most critical wound site needing treatment. However, it could also be selected based on other factors such as location in relation to the other wound sites and/or distance from the pressure sources. Thus, for purposes of the present disclosure, the wound dressing 16A in which the connection bridge 150 is connected may also be referred to as the connection site 16A. To connect the bridge 100 to additional wound dressings 16B and 16C that are generally able to be disposed along the same line of a patient's skin with respect to the connection site 16A, one or more dual lumen extension elements 180A, 180B, 180C are fluidly coupled to the connection bridge 150. According to this embodiment, the first lumen 182A, 182B of the dual lumen extension elements 180A, 180B include one or more fluid adapters 188A, 188B disposed along the length of the first lumens 182A, 182B for fluidly coupling the first fluid flow path 32 to wound dressings 16B and 16C. The first lumen 182C of the dual extension element 180C then connects the first fluid flow path 32 to the reduced pressure tubing 14. To extend the second fluid flow path 42, the second lumens 192A, 192B, 192C of dual extension elements 180A, 180B, 180C are similarly fluidly coupled to the connection bridge 150 and the secondary pressure tubing 24.

With reference to FIG. 8, a similar set-up as FIG. 7 is shown in which bridge 100 includes dual lumen extension elements 180A, 180B, 180C. However, according to this embodiment, instead of fluid adapters 188A, 188B being connected to wound dressings 16B, 16C, fluid adapters 188A, 188B are first connected to respective single lumen extension elements 200A, 200B that are in-turn connected to branched-off wound dressings 16B, 16C using fluid adapters 208A, 208B.

In yet another exemplary set-up as shown in FIG. 9, a plurality of single lumen extension elements may be used to fluidly couple the first fluid flow path 32 to wound dressings 16B, 16C that are not positioned on a direct line with respect to connection site 16A. According to this embodiment, single lumen extension elements 200A, 200B include one or more fluid adapters 208A, 208B disposed along the length of the single lumen extension elements 200A, 200B for fluidly coupling the first fluid flow path 32 to wound dressings 16B, 16C. Single lumen extension element 200C then brings the first fluid flow path 32 back along the line between the reduced pressure tubing 14 and the connection site 16A. Single lumen extension elements 200D, 200E are then used to extend the second fluid flow path 42 to a common point aligned with single lumen extension element 200C. At that point, a dual lumen extension element 180 is used to fluidly connect the first fluid flow path 32 to the reduced pressure tubing 14 and the second fluid flow path 42 to the secondary pressure tubing 24.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A system for facilitating delivery of reduced pressure to a wound site, the system including a bridge comprising:
    a first sealing member having an inner surface and an outer surface;
    a second sealing member having an inner surface and an outer surface, wherein a portion of the inner surface of the second sealing member is sealed to a portion of the inner surface of the first sealing member, thereby forming a sealed enclosure between the first and second sealing members;
    the sealed enclosure comprising a reduced pressure lumen, a secondary pressure lumen, and a manifold member disposed between the reduced pressure lumen and the secondary pressure lumen; and
    the reduced pressure lumen having a first end and a second end, the first end of the reduced pressure lumen configured to be fluidly coupled to reduced pressure tubing that is fluidly coupled to a reduced pressure source;
    the secondary pressure lumen having a first end and a second end, the first end of the secondary pressure lumen configured to be fluidly coupled to secondary pressure tubing that is fluidly coupled to a secondary pressure source, and the second end of the secondary pressure lumen being fluidly coupled to the second end of the reduced pressure lumen to facilitate flow of exudate removed from the wound site by the reduced pressure source using the secondary pressure source; and
    one or more fluid adapters operable to be connected to a wound dressing disposed at the wound site, the one or more fluid adapters positioned and configured with respect to the reduced pressure lumen to apply reduced pressure from the reduced pressure lumen to the wound site through the wound dressing and to deliver exudate removed from the wound site through the reduced pressure lumen to the reduced pressure tubing, the one or more fluid adapters including:
        a first fluid adapter disposed adjacent to the second end of the reduced pressure lumen for connection to the wound dressing; and
        a second fluid adapter disposed adjacent to the second end of the secondary pressure lumen for connection to the wound dressing,
    wherein the secondary pressure lumen is fluidly coupled to the reduced pressure lumen based at least in part on a converged fluid flow path in the wound dressing.

2. The system of claim 1, wherein at least one of the one or more fluid adapters extend through the first sealing member.

3. The system of claim 1, wherein the first sealing member is configured to contact skin of a patient, the first sealing member including a moisture permeable membrane for allowing moisture from the patient to transfer into at least one of the reduced pressure lumen and the secondary pressure lumen through the moisture permeable membrane.

4. The system of claim 1, wherein the first sealing member is configured to adhere to skin of a patient, the first sealing member including a release liner for covering the first sealing member prior to securing the bridge to the skin of the patient.

5. The system of claim 4, wherein the release liner includes a plurality of perforated sections for providing selective application of the first sealing member to the skin of the patient.

6. The system of claim 1, further comprising:
    the reduced pressure source configured to deliver the reduced pressure through the reduced pressure tubing;
    a canister fluidly coupled with the reduced pressure source and the reduced pressure tubing for receiving exudate collected from the wound site; and
    the secondary pressure source configured to deliver the secondary pressure through the secondary pressure tubing.

7. The system of claim 6, further comprising a first closed volume disposed between and including the reduced pressure source and the second end of the reduced pressure lumen of the bridge, and a second closed volume disposed between and including the secondary pressure source and the second end of the secondary pressure lumen of the bridge, the first closed volume and the second closed volume being fluidly connected at the second ends of the reduced pressure lumen and the secondary pressure lumen.

8. The system of claim 7, wherein the first closed volume includes a first pressure sensor and the second closed volume includes a second pressure sensor.

9. The system of claim 6, further comprising a controller configured to communicate with the secondary pressure source for selectively delivering the secondary pressure to the secondary pressure lumen of the bridge.

10. A system for facilitating delivery of reduced pressure to a wound site, the system including a bridge comprising:
a first sealing member having an inner surface and a skin contacting outer surface;
a second sealing member sealed to a portion of the inner surface of the first sealing member for forming a sealed enclosure having a reduced pressure lumen and a secondary pressure lumen disposed between the first sealing member and the second sealing member, the secondary pressure lumen being fluidly coupled to the reduced pressure lumen to form a fluid flow path within the sealed enclosure; and
a first fluid adapter for fluidly coupling the reduced pressure lumen to a reduced pressure source to deliver exudate removed from the wound dressing through the reduced pressure lumen of the fluid flow path;
a second fluid adapter for fluidly coupling the secondary pressure lumen to a secondary pressure source such that, when the secondary pressure source is activated, fluid flow from the secondary pressure source delivered through the secondary pressure lumen converges with fluid flow from the reduced pressure source along the fluid flow path to facilitate delivery of the exudate removed from the wound dressing through the reduced pressure lumen; and
a third fluid adapter extending through the first sealing member and disposed along the fluid flow path between the first fluid adapter and the second fluid adapter for fluidly coupling the reduced pressure lumen to the wound dressing and for fluidly coupling the secondary pressure lumen to the reduced pressure lumen adjacent to the wound dressing.

11. The system claim 10, wherein the first sealing member is formed at least in part of a moisture permeable membrane comprising an air-impermeable film that allows moisture from a patient to transfer into the sealed enclosure through the first sealing member while maintaining reduced pressure at the wound site.

12. The system of claim 11, wherein the bridge adheres to skin of the patient, the bridge further comprising a release liner for covering the skin contacting outer surface, wherein the release liner is configured to be removed from the skin contacting outer surface prior to securing the bridge to the skin of the patient.

13. The system of claim 12, wherein the release liner includes a plurality of perforated sections separated by perforations so that selected ones of the plurality of perforated sections can be removed from the skin contacting surface, thereby providing for selective application of the skin contacting outer surface to the skin of the patient.

14. A bridge for facilitating delivery of reduced pressure to a wound site, the bridge comprising:
a first sealing member having a top surface and a bottom surface;
a second sealing member having a top surface and a bottom surface, wherein a portion of the bottom surface of the second sealing member is sealed to a portion of the top surface of the first sealing member, thereby forming a sealed enclosure between the first and second sealing members;
the sealed enclosure comprising:
a reduced pressure lumen and a secondary pressure lumen disposed in a side-by-side arrangement on the top surface of the first sealing member;
a manifold member disposed on the top surface of the first sealing member between the reduced pressure lumen and the secondary pressure lumen; and
an opening in the manifold that fluidly couples the secondary pressure lumen to the reduced pressure lumen to form a fluid flow path within the sealed enclosure,
wherein the reduced pressure lumen has a first end and a second end, the first end of the reduced pressure lumen being configured to be fluidly coupled to reduced pressure tubing that is fluidly coupled to a reduced pressure source,
wherein the secondary pressure lumen has a first end and a second end, the first end of the secondary pressure lumen being configured to be fluidly coupled to secondary pressure tubing that is fluidly coupled to a secondary pressure source, and
wherein the second end of the secondary pressure lumen is fluidly coupled to the second end of the reduced pressure lumen through the opening in the manifold member to facilitate flow of exudate removed from the wound site; and
one or more fluid adapters operable to be connected to a wound dressing disposed at the wound site, the one or more fluid adapters positioned and configured with respect to the reduced pressure lumen to apply reduced pressure from the reduced pressure lumen to the wound site through the wound dressing and to deliver exudate removed from the wound site through the reduced pressure lumen to the reduced pressure tubing.

15. The bridge of claim 14, wherein at least one of the one or more fluid adapters extend through the first sealing member and at least one of the one or more fluid adapters is disposed adjacent to the opening of the manifold member.

16. The bridge of claim 14, wherein the first sealing member is configured to contact skin of a patient, the first sealing member including a moisture permeable membrane for allowing moisture from the patient to transfer into at least one of the reduced pressure lumen and the secondary pressure lumen through the moisture permeable membrane.

17. The bridge of claim 14, wherein the first sealing member is configured to adhere to skin of a patient, the first sealing member including a release liner for covering the first sealing member prior to securing the bridge to the skin of the patient.

* * * * *